United States Patent [19]
Prutchi et al.

[11] Patent Number: 5,722,998
[45] Date of Patent: Mar. 3, 1998

[54] APPARATUS AND METHOD FOR THE CONTROL OF AN IMPLANTABLE MEDICAL DEVICE

[75] Inventors: David Prutchi; Patrick J. Paul, both of Lake Jackson; David G. Genzer, Bay City, all of Tex.

[73] Assignee: Intermedics, Inc., Angleton, Tex.

[21] Appl. No.: 475,491

[22] Filed: Jun. 7, 1995

[51] Int. Cl.$^6$ .................................................. A61N 1/36
[52] U.S. Cl. .................................. 607/30; 607/59
[58] Field of Search .................. 607/9, 27, 30, 607/32, 59, 60

[56] References Cited

U.S. PATENT DOCUMENTS

| | | | |
|---|---|---|---|
| 3,631,860 | 1/1972 | Lopin | 607/30 |
| 4,102,345 | 7/1978 | Cannon, III | 607/27 |
| 4,126,139 | 11/1978 | Walters et al. | 607/30 |
| 4,424,812 | 1/1984 | Lesnick | 607/30 |
| 4,903,699 | 2/1990 | Baker, Jr. et al. | |
| 4,967,746 | 11/1990 | Vandegriff | |
| 5,292,342 | 3/1994 | Nelson et al. | |
| 5,304,206 | 4/1994 | Baker, Jr. et al. | |
| 5,438,990 | 8/1995 | Wahlstrand et al. | 607/9 |

OTHER PUBLICATIONS

Integrated GMR Magnetic Sensors Series, Advance Release, NVSI Series, Nonvolatile Electronics, Inc., High Sensitivity, Small Size, p. –2.

Rapid Prototype Integrated GMR Magnetic Sensors, Nonvolatile Electronics, Inc., pp. 1–2.

GMR Magnetic Bridge Sensor, Nonvolatile Electronic, Inc., pp. 1–2.

GMR Materials: Theory and Applications, Sensors, Sep. 1994, David Prutchi, Ph.D., pp. 42–48.

Science & Technology Physics, Magnetic Field of Dreams, Business Week/Apr. 18, 1994, pp. 118–120.

The Constant Current Loop: A New Paradigm for Resistance Signal Conditioning, Karl F. Anderson, NASA Dryden Flight Research Center, Sensors and Systems, Sensors, Apr. 1994, pp. 34–38.

Giant Magnetoresistance Technology Paves The Way for Magnetic Field Sensing, Technology Advics, Electronics Design, Nov. 21, 1994.

*Primary Examiner*—William E. Kamm
*Attorney, Agent, or Firm*—Mark R. Wisner

[57] ABSTRACT

An implantable medical device includes a giant magnetoresistance ratio (GMR) sensor is used to detect the presence of a magnet in order to command the device to enter a predetermined mode of operation. The GMR responds to a modulated magnetic field generated by the programming of a command transmitter apparatus for non-invasive programming or controlling of the implanted device. The implantable medical device also monitors for the presence of a steady magnetic field to place the implanted device in a known, safe mode.

3 Claims, 4 Drawing Sheets

APPARATUS AND METHOD FOR THE CONTROL OF AN IMPLANTABLE MEDICAL DEVICE

BACKGROUND OF THE INVENTION

The present invention relates generally to the field of implantable medical devices such as cardiac pacemakers, defibrillators, cardioverters, drug delivery devices, neural stimulators, and the like. More particularly, the present invention relates to a method and apparatus for controlling the output and mode of operation of such devices and changing the output and/or mode of operation of such devices with an external signal source, e.g., without an invasive process.

FIELD OF THE INVENTION

Many modern pacemakers adjust pacing rate in response to a patient's intrinsic electrical cardiac activity and/or other parameters such as a patient's metabolic demand for oxygen. Most state-of-the-art pacemakers are programmable or multi-programmable, such as with an external programmer which communicates with the implanted device via radio frequency (Rf) telemetry. A pacemaker may be programmable with respect to various parameters including pacing mode, pacing rate, stimulating pulse width, refractory period, sense amplifier sensitivity, rate-responsiveness to measured physiological parameters, and other parameters.

Implantable devices, such as pacemakers, are typically programmed by broadcasting information to the device in the form of digital information identifying at least the parameter to be programmed and the desired parameter value that will be input as a result of the programming. This information is typically in the form of binary digital data which is radio-frequency modulated and transmitted to an antenna within the implanted device. In the implanted device, the signal is demodulated and the digital information decoded. Other information, such as an identification code for the implanted device, verification codes, error correction codes, access verification codes, and the like, may also be transmitted to the device during programming. In addition, the transmitted information may include initialization data to reduce the possibility of inadvertent programming (or re-programming) of the device. Alternatively, a reed switch may be provided which allows for limited external control, such as for actuation of a programming mode, by means of placing an external magnet in proximity to the switch for actuation thereof.

The disadvantages of the radio-frequency system of such devices are characterized in detail in U.S. Pat. No. 5,292,342, and the present invention is intended in part to overcome those disadvantages, as well as certain shortcomings of the device disclosed in the '342 patent.

The '342 patent describes a device incorporating a MAGFET sensor in a circuit including a logic circuit for generating two signals ("magnet present" or "magnet not present"), depending upon the orientation of the magnetic field, which signals comprise essentially digital data, sensing different numbers of removal/replacement cycles of the external magnet thereby identifying the different operating parameters of the device for programming that device. The present invention, however, adds to the programming and operating capabilities of such devices by providing additional programming options and/or input and allows marking by the patient of external stimuli and/or operating conditions. These objects of the present invention are achieved by using a so-called giant magnetoresistance ratio (GMR) sensor in the device and external magnetic fields to which that sensor is sensitive.

The device disclosed in U.S. Pat. No. 5,292,342 is characterized by other disadvantages and limitations. For instance, exclusive use of that sensor and an external magnetic field for programming limits that device to receiving only communications from the outside; without radio-frequency circuitry, and thus the device is not capable of transmitting signals. Further, and perhaps more importantly, the programming options that are available for that device are limited.

In accordance with the present invention, it has been discovered that GMR sensors are adaptable for a number of control functions other than re-programming of an implantable device including a MAGFET in the manner described in U.S. Pat. No. 5,292,342. Specifically, it is an object of the present invention to supplement the programming and operating modes of an implantable device such as a pacemaker by providing, in addition to radio-frequency telemetry, a second mode of communication to the implantable device which is less likely to be influenced by external electromagnetic fields and which offers greater operating and programming flexibility to the device.

It is also an object of the present invention to include in this operating and programming flexibility the opportunity for patient input for subsequent downloading by radio-frequency telemetry for diagnostic and other purposes relating to the function of the device.

SUMMARY OF THE INVENTION

The present invention solves these shortcomings of the prior art and provides these objects. This invention includes an implantable biomedical device in which a giant magnetoresistance ratio (GMR) sensor is used to detect the presence of a magnet in order to command the device to enter a predetermined mode of operation. Further, the GMR responds to a modulated magnetic field generated by the programming of a command transmitter apparatus for non-invasive programming or controlling of the implanted device.

The present invention also uses sensed, time varying magnetic signals which indicate low frequency electromagnetic noise. Such electromagnetic noise may adversely influence the behavior of an implantable medical device which has sensitive signal sensing circuits, as described in concurrently filed U.S. application Ser. No. 08/475,489 entitled Electromagnetic Noise Detector For Implantable Medical Devices. The GMR sensor signal, when appropriately conditioned and demodulated, may be used for the detection of extraneous low-frequency electromagnetic fields that may cause unreliable or unsafe operation of the implantable device. For example, a pulsed magnetic field from a electronic article surveillance system (EAS) may interfere with normal operation of an implantable medical device. The implantable medical device may then activate special circuitry to enter a safe mode of operation. A plurality of spaced GMR sensors may be employed in the present invention to counteract the effects of multiple axis magnetic fields encountered by a mobile recipient of such an implantable device.

In the present invention, a GMR sensor is excited by an excitation voltage source. The GMR sensor develops a modulated signal in response to an applied magnetic field and provides this modulated signal to a sensor signal conditioning circuit. The sensor signal conditioning circuit amplifies and filters the GMR sensor signal such that the circuit's output is a demodulated version of the applied magnetic field. The demodulated version of the applied field is used by a command decoder circuit, which decodes modulated signals into commands for the implantable device. Also, the present invention detects the application of a permanent magnet for appropriate reversion to a magnet response mode of operation.

These and other objects and advantages of the present invention will be immediately apparent to those of skill in the art from a review of the following detailed description along with the accompanying drawings.

DETAILED DESCRIPTION OF A PREFERRED EMBODIMENT

Figure 1:
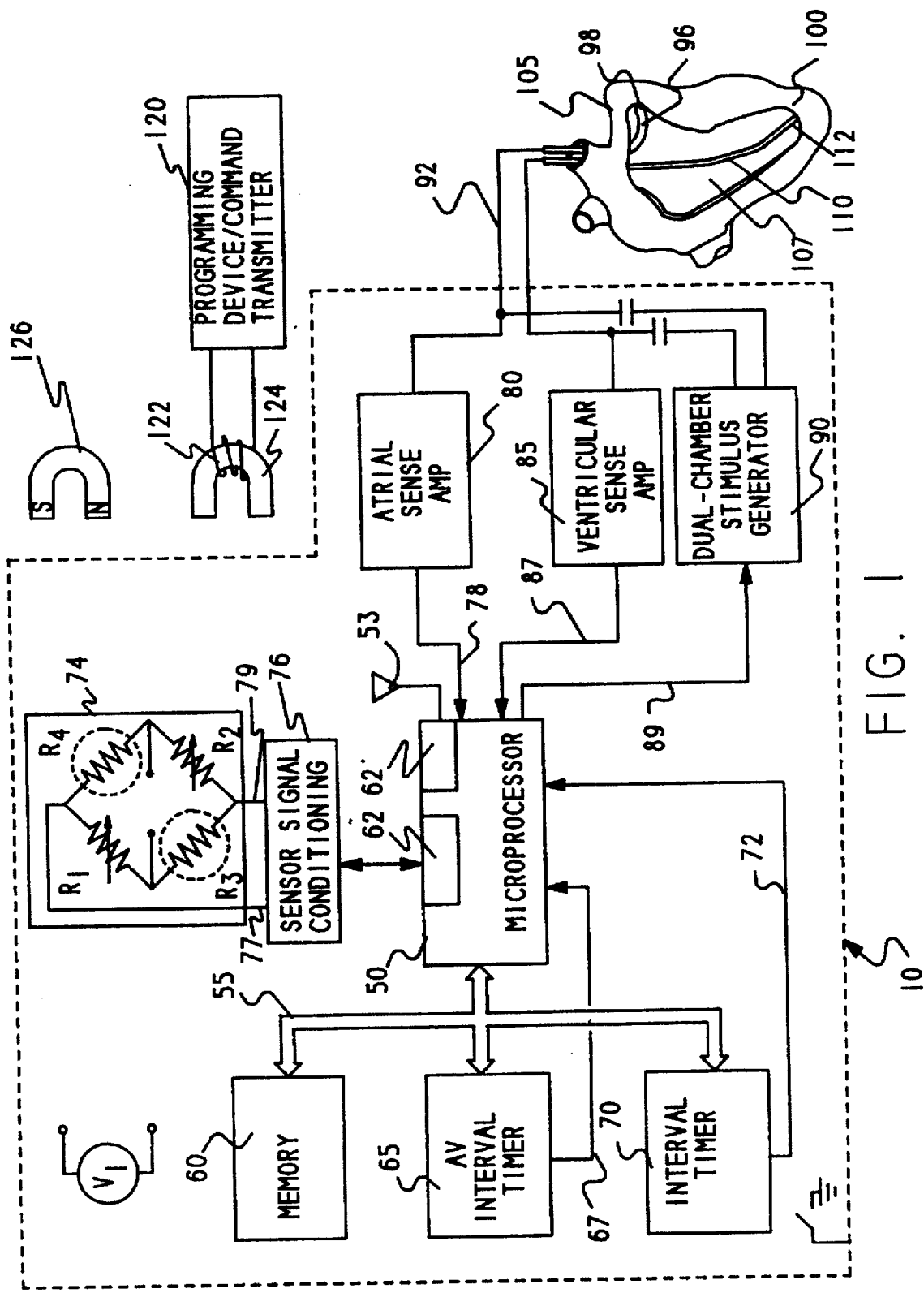
FIGS. 1a and 1b are block diagrams of a pacemaker having circuitry for controlling the pacemaker in accordance with a preferred embodiment of the present invention.
Figure 1A:
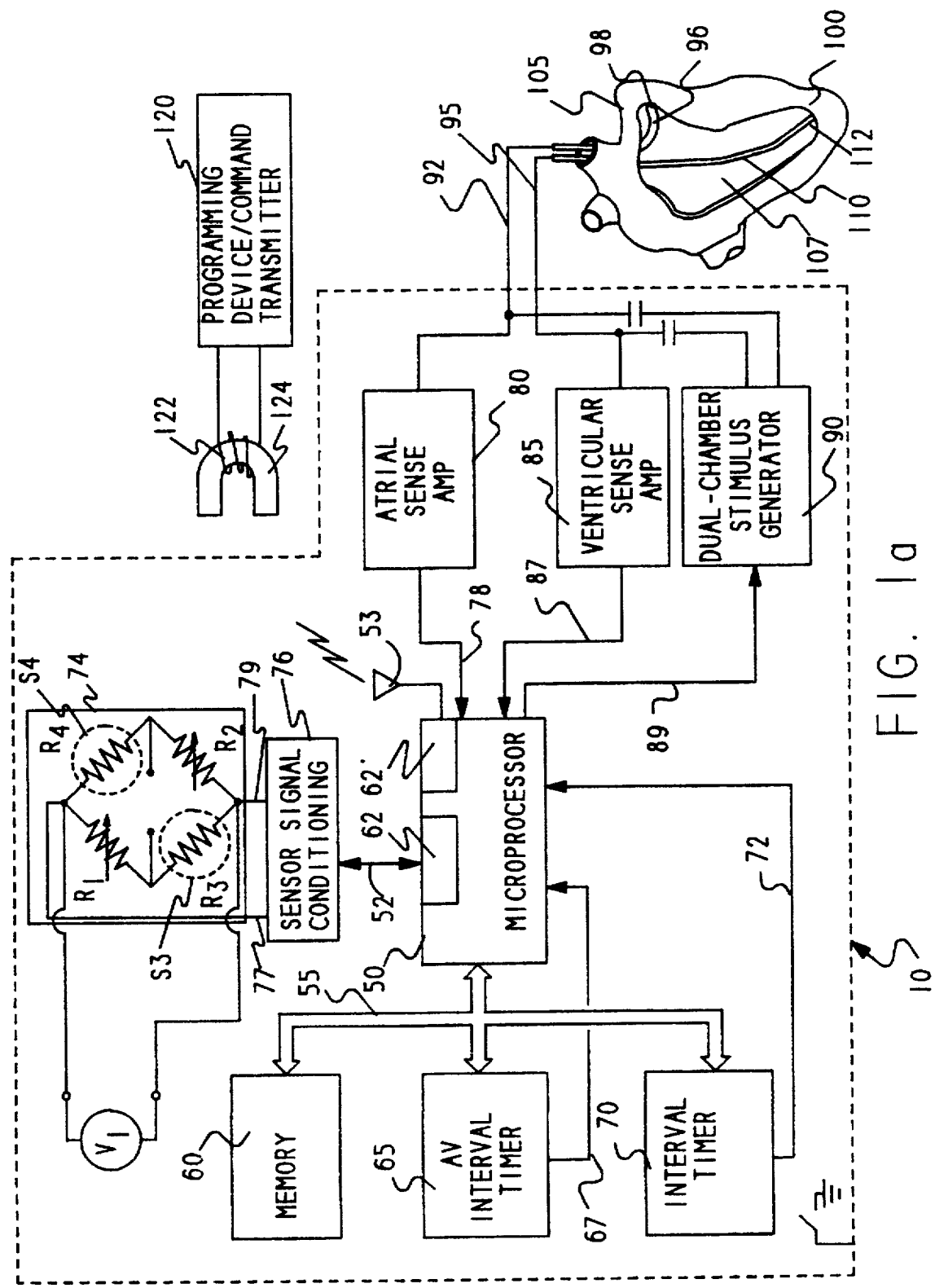

FIG. 1a is a block diagram representing a rate adaptive pacemaker 10 for control in accordance with a presently preferred embodiment of the present invention. Those skilled in the art who have the benefit of this disclosure, however, will recognize that the present invention is adaptable for use in controlling other types of pacemakers and many other types of implantable, microprocessor-controlled medical devices. The pacemaker 10 is illustrated merely for purposes of exemplifying a presently preferred embodiment of the invention.

Briefly, U.S. Pat. No. 4,967,746 describes a pacemaker controlled by a microprocessor 50 such as the microprocessor described in detail in U.S. Pat. No. 4,404,972, incorporated herein in its entirety by this specific reference thereto and assigned to the Assignee of the present invention. The basic pacemaker described in the '746 patent has been modified and improved by the present invention as described below.

The microprocessor 50 is provided with input/output ports connected in a conventional manner via bi-directional bus 55 to memory 60, an A-V interval timer 65, and a pacing interval timer 70. In addition, the A-V timer 65 and pacing interval timer 70 each has an output connected individually to a corresponding input port of the microprocessor 50 by lines 67 and 72, respectively.

The microprocessor 50 preferably also has an input/output port connected to a telemetry interface 62 by line 52. The pacemaker 10 when implanted is thus able to receive pacing and rate control parameters from an external programmer 120 (FIG. 2) and send data to an external receiver as known in the art, and described below with regard to an antenna 53. One such system and encoding arrangement is described in U.S. Pat. No. 4,539,992, which is also assigned to the assignee of the present invention and which is incorporated herein in its entirety by this specific reference thereto. The microprocessor 50 may also be provided with a radiofrequency link through the antenna 53. The antenna 53 is coupled to a telemetry interface 62', which may be the same interface as interface 62, or it may provide a distinct interface.

The microprocessor output ports are connected to the inputs of a dual chamber stimulus pulse generator 90 by control line 89. The microprocessor 50 transmits pulse parameter data, such as amplitude and pulse width, as well as enable/disable initiation codes to the generator 90 on control line 89.

The microprocessor 50 also has input ports connected to outputs of an atrial sense amplifier 80 and a ventricular sense amplifier 85 by lines 78 and 87, respectively. The atrial and ventricular sense amplifiers 80 and 85 detect occurrences of P-waves and R-waves, respectively. The atrial sense amplifier 80 outputs a signal on line 78 to the microprocessor 50 when it detects a P-wave and the ventricular sense amplifier 85 outputs a signal on line 87 to the microprocessor 50 when it detects an R-wave.

The input of the atrial sense amplifier 80 and the output of the stimulus pulse generator 90 are connected to a first conductor 92 which is inserted in a first conventional lead 96. Lead 96 is inserted into the heart 100 and has an electrically conductive pacing/sensing tip 98 at its distal end which is electrically connected to the conductor 92. The pacing/sensing tip 98 is preferably lodged in the right atrium 105.

The input of the ventricular sense amplifier 85 and the output of stimulus pulse generator 90 are connected to a second conductor 95. The second conductor 95 is inserted in a second conventional lead 110 which is inserted intravenously or otherwise in the right ventricle 107 of the heart 100. The second lead 110 has an electrically conductive pacing/sensing tip 112 at its distal end. The pacing/sensing tip 112 is electrically connected to the conductor 95. The pacing)sensing tip 112 is preferably lodged on the wall of the right ventricle.

The conductors 92 and 95 conduct the stimulus pulses generated by the stimulus pulse generator 90 to the respective pacing/sensing tips 98 and 112. The pacing/sensing tips 98 and 112 and corresponding conductors 92 and 95 also conduct sensed cardiac electrical signals in the right atrium appendage and right ventricle to the atrial and ventricular amplifiers 80 and 85, respectively.

The implantable device 10 further includes a magnetic sensor 74. The sensor 74 may be any appropriate sensor capable of sensing a time-varying magnetic field, in a manner described herein, and is preferably a GMR sensor. The sensor 74 is excited by an excitation voltage source $V_1$. The GMR is preferably an integrated GMR magnetic sensor from Nonvolatile Electronics, Inc. in Eden Prairie, Minn. Other resistive sensor geometries are equally applicable to the present invention, such as those described in The Constant Current Loop: A New Paradigm for Resistance Signal Conditioning, Anderson, K. F., Sensors, April 1994, so long as such resistive sensors are sensitive to a time-varying magnetic field.

Figure 1B:
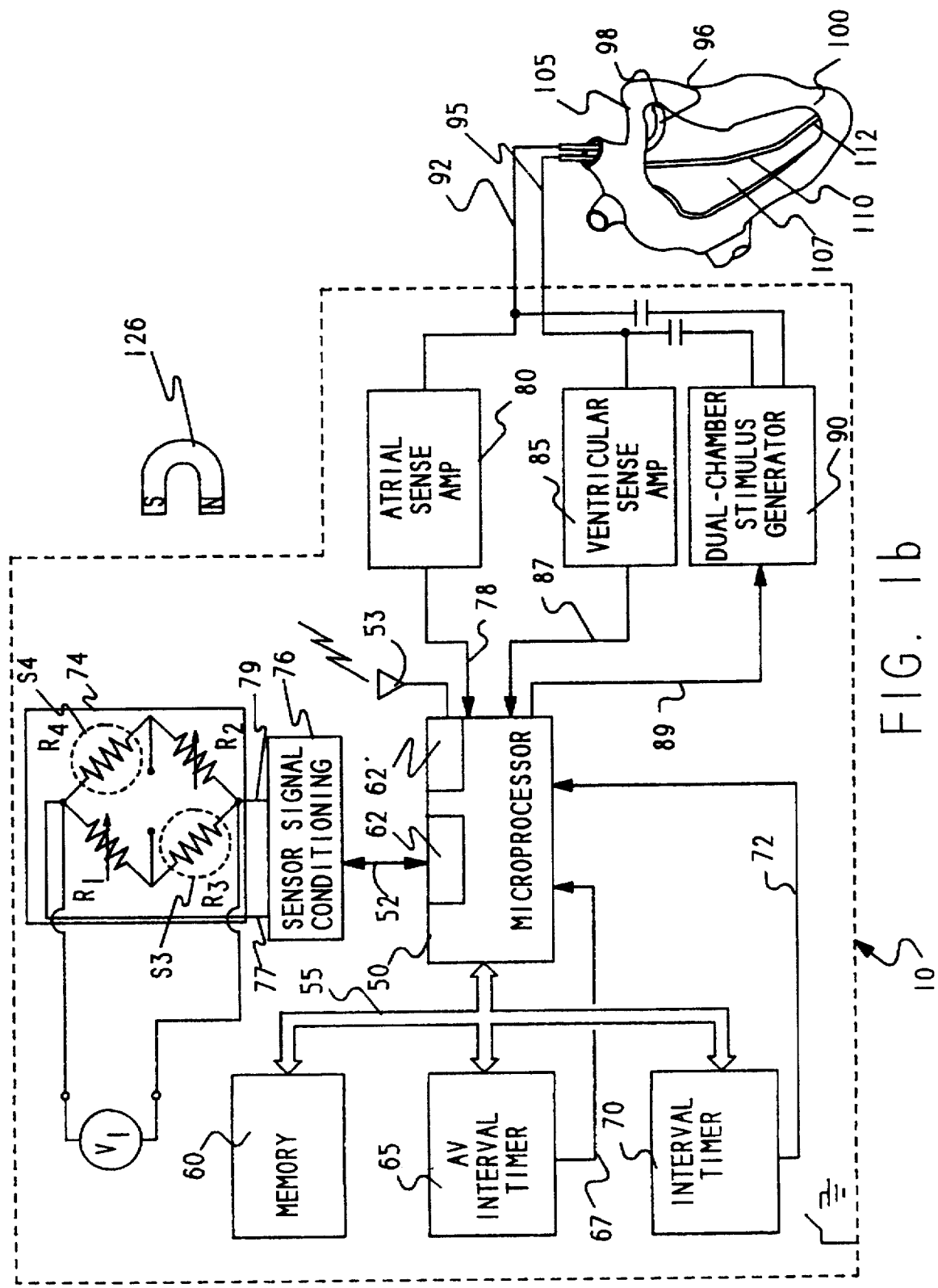

As shown in FIGS. 1a and 1b, the GMR may be arranged as a bridge circuit with bridge elements $R_1$–$R_4$, inclusive. The GMR sensor provides an output signal to a sensor signal conditioning circuit 76 via signal lines 77 and 79. This signal conditioning circuit 76 demodulates the signal from the GMR sensor 74, as well as providing filtering and signal shaping so that the signal is in condition for use by the microprocessor 50. The sensor signal conditioning circuit provides a further feature of defining a minimum threshold level from the sensor 74 to eliminate the deleterious effects of magnetic noise.

Figure 3:
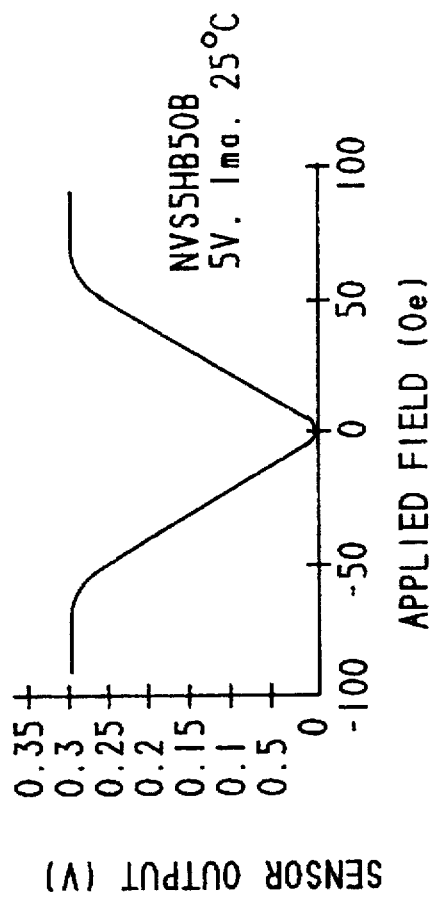
FIG. 3 is a plot of the operating characteristics of a typical giant magnetoresistance ratio sensor, as applied in accordance with the present invention.

The bridge elements $R_1$–$R_4$ are preferably integrated circuit field effect transistors that have been biased to operate in the resistive region. Two of the bridge elements, for example $R_3$ and $R_4$, are shielded against magnetic influence, by shields $S_3$ and $S_4$ while magnetically-sensitive $R_1$ and $R_2$ are unshielded. FIG. 3 illustrates typical operating characteristics of the GMR sensor 74 in the presence of a magnetic field, with the output of the sensor between lines 77 and 79. As shown, the output voltage of the sensor is independent of the polarity of the magnetic field; that is, the voltage output depends only on the absolute value of the magnetic field.

The magnetic field is provided to the implantable device 10 from a source outside the patient. In a preferred embodiment, the magnetic signal is provided by a programming device/command transmitter 120, shown in greater detail in FIG. 2. The command transmitter 120 powers a coil 122 which is magnetically coupled to a core 124. The command transmitter 120 develops a modulated digital data stream which is magnetically coupled to the sensor 74 for communication to the microprocessor 50. The digital data stream may include a code sequence to define a specific parameter, which then follows the code sequence in the data stream. In this way, commands or information may be selectively directed to the microprocessor. If desired this may include re-programming the implantable device 10, to suit the needs of the patient.

The implantable device 10 is also sensitive to the presence of a magnetic field from a permanent magnet 126, shown in FIG. 1b. Thus, the sensor 74 may be used to revert the operation of the implantable device to the magnet mode of operation. In magnet mode, a predetermined, typically asynchronous, ventricular pacing rate is issued. This mode eliminates complex timing and synchronizing signals to assist in monitoring the functioning of a remotely stimulated organ. As used herein, the term "magnet mode" may also be referred to as a "known, safe mode" because this mode is dependent only on the voltage of the battery in the implanted device, and is not dependent on either heart activity or on any adapted rate factors which can alter operation of the implanted device.

Figure 2:
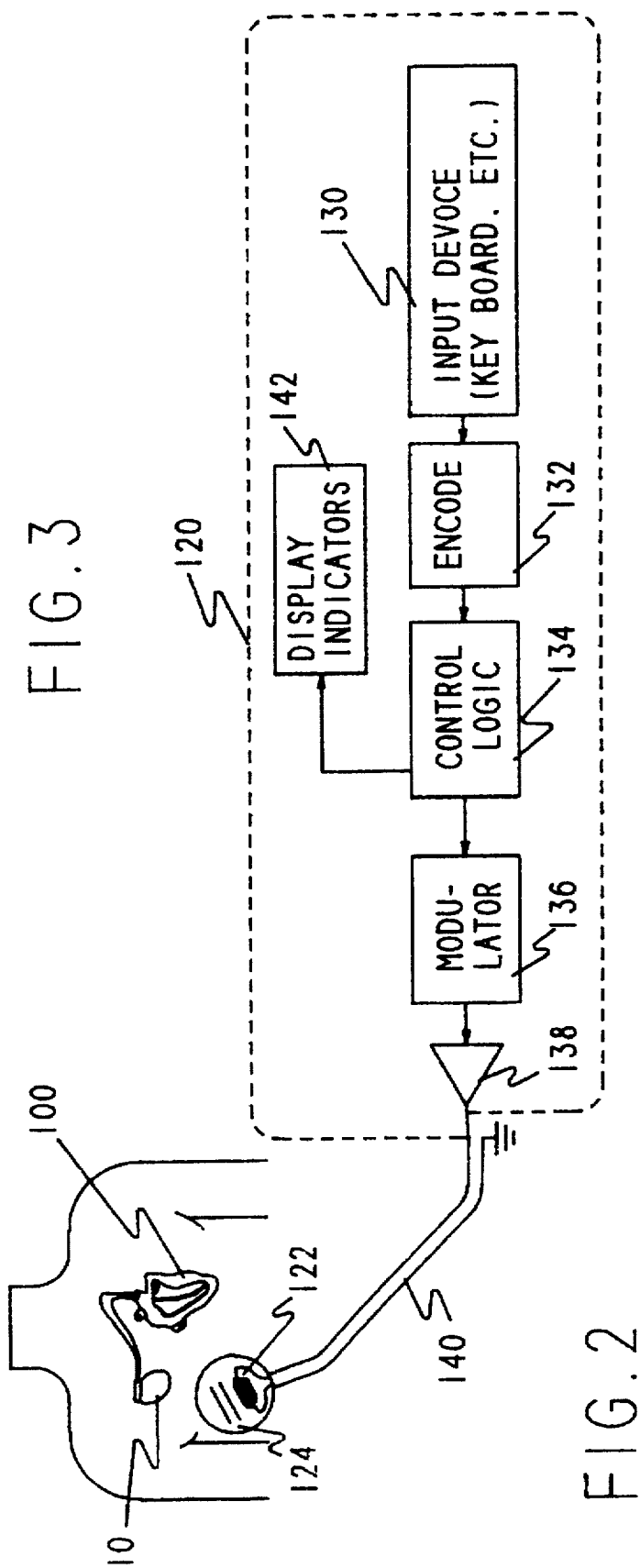
FIG. 2 is a block diagram and schematic representation of the external transmitter for programming the pacemaker of FIGS. 1a and 1b.

FIG. 2 depicts a preferred embodiment of the programming device/command transmitter 120 of the present invention. An input device 130, such as a keyboard, switch array, modem, or other means of assembling a character stream, is coupled to an encoding element 132 which develops the digital bit string. This bit string is communicated to a control logic element 134 which drives a modulator 136. The modulator modulates the signal from the control logic to a condition to drive an output stage or amplifier 138. The amplifier 138 matches the impedance of a conductor 140 and amplifies the signal sufficiently to drive the coil 122 and core 124 to develop a magnetic signal that is detected by the device 10. The control logic 134 also provides monitoring of the transmitter 120 for display indicators 142.

The principles, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

We claim:

1. A device for altering the operation of a medical apparatus, a portion of the device of which is configured to be implanted within a human, the device comprising:

a. a command transmitter for generating a digital bit string;

b. an electromagnet coupled to the command transmitter to develop a series of magnetic pulses corresponding to the digital bit string;

c. an implantable giant magnetoresistance ratio sensor capable of sensing a time-varying magnetic field, to receive the series of magnetic pulses and develop an output signal;

d. a microprocessor;

e. an implantable sensor signal conditioner electrically coupled to the microprocessor to receive the output signal from the sensor and develop a signal in a condition for use by the microprocessor; and f. means to modify the operation of the microprocessor based upon the signal developed by the signal conditioner.

2. In an apparatus comprising a medical device implantable in a human and means of communicating with the implanted medical device, the implantable medical device including a processor programmed to define predetermined operating parameters of the medical device, a method of altering the operating parameters comprising the steps of:

a. developing a digital bit string representative of a command for communication to the medical device;

b. driving an electromagnet to produce a digital series of magnetic pulses representative of the digital bit string;

c. receiving the series of magnetic pulses in a giant magnetoresistance ratio sensor in the medical device to develop a modulated output voltage;

d. conditioning the modulated output from the sensor to produce a conditioned bit stream;

e. receiving the conditioned bit stream in the processor in the medical device to alter the operating parameters of the medical device; and f. altering the programming of the processor based upon the received conditioned bit stream.

3. A device for altering the operation of a medical apparatus, a portion of the device of which is configured to be implanted within a human, the device comprising:

a. a command transmitter for generating a steady magnetic field;

b. an implantable giant magnetoresistance ratio sensor capable of sensing the presence of the steady magnetic field to develop an output command signal to place the apparatus in a known, safe mode; and c. and implantable sensor signal conditioner to receive the output command signal from the sensor and issue a magnet mode signal to the medical device.

* * * * *